(12) United States Patent
Urban et al.

(10) Patent No.: US 10,806,096 B2
(45) Date of Patent: Oct. 20, 2020

(54) METHOD FOR STIMULATING THE RESISTANCE OF PLANTS TO BIOTIC STRESS BY UV RADIATION EXPOSURE

(71) Applicants: UNIVERSITE D'AVIGNON ET DES PAYS DU VAUCLUSE, Avignon (FR); UNIVERSITE DE MONTPELLIER, Montpellier (FR); CENTRE NATIONAL DE LA RECHERCHE SCIENTIF, Paris (FR)

(72) Inventors: Laurent Urban, Molleges (FR); Jawad Aarrouf, Le Pontet (FR); Dounyazade Chabane Sari, Montpellier (FR); Bernard Orsal, Les Matelles (FR)

(73) Assignees: UNIVERSITE D'AVIGNON ET DES PAYS DU VAUCLUSE, Avignon (FR); UNIVERSITE DE MONTPELLIER, Montpellier (FR); CENTRE NATIONAL DE LA RECHERCHE SCIENTIF, Paris (FR)

( * ) Notice: Subject to any disclaimer, the term of this patent is extended or adjusted under 35 U.S.C. 154(b) by 280 days.

(21) Appl. No.: 15/760,744

(22) PCT Filed: Sep. 16, 2016

(86) PCT No.: PCT/EP2016/072064
§ 371 (c)(1),
(2) Date: Mar. 16, 2018

(87) PCT Pub. No.: WO2017/046389
PCT Pub. Date: Mar. 23, 2017

(65) Prior Publication Data
US 2018/0255710 A1    Sep. 13, 2018

(30) Foreign Application Priority Data
Sep. 17, 2015  (EP) .................................. 15306432

(51) Int. Cl.
*A01G 7/04* (2006.01)
*A01G 7/06* (2006.01)
(Continued)

(52) U.S. Cl.
CPC ............... *A01G 7/045* (2013.01); *A01G 7/06* (2013.01); *A01H 3/02* (2013.01); *A01H 5/08* (2013.01); *A01H 5/12* (2013.01); *Y02P 60/14* (2015.11)

(58) Field of Classification Search
CPC .................................. A01G 7/045; A01H 3/02
See application file for complete search history.

(56) References Cited

U.S. PATENT DOCUMENTS

| | | | | |
|---|---|---|---|---|
| 4,380,551 A | * | 4/1983 | Frontczak | ................ A01G 7/00 111/900 |
| 5,040,329 A | * | 8/1991 | Michaloski | ............ A01G 7/045 47/1.1 |

(Continued)

FOREIGN PATENT DOCUMENTS

| EP | 2 272 324 | 12/2011 | | |
|---|---|---|---|---|
| EP | 2887053 A1 | * 6/2015 | ............... | A01G 7/00 |

(Continued)

OTHER PUBLICATIONS

Gustafsson et al. "Pathogenic variation and sexual reproduction in Swedish populations of Bremia lactucae" Theor Appl Genet. Sep. 1985;70(6):643-9. doi: 10.1007/BF00252290. (Year: 1985).*

(Continued)

*Primary Examiner* — Magdalena Topolski
*Assistant Examiner* — Morgan T Barlow
(74) *Attorney, Agent, or Firm* — Hauptman Ham, LLP (57) ABSTRACT

The present invention relates to a method for stimulating the resistance of plants to biotic stress by radiation exposure of at least one spot of a plant characterized in that the radiation (Continued)

exposure is performed by UV-C rays alone or UV-B rays alone or a combination thereof with an exposure duration being less or equal to one second and the radiation exposure being repeated at least once with an interval of time between one hour and one month.

The invention will find an application for stimulating natural defenses of plants to biotic stress as pests, bacteria, fungus or virus. The invention could be used directly on plants growing in fields for agriculture and the food industry.

20 Claims, 7 Drawing Sheets

(51) Int. Cl.
　　*A01H 3/02*　　(2006.01)
　　*A01H 5/08*　　(2018.01)
　　*A01H 5/12*　　(2018.01)

(56) References Cited

U.S. PATENT DOCUMENTS

| | | | | |
|---|---|---|---|---|
| 5,718,080 | A * | 2/1998 | Ohtani | A01G 7/045 47/58.1 R |
| 6,309,440 | B1 * | 10/2001 | Yamashita | A01G 7/06 47/57.6 |
| 2008/0298052 | A1 * | 12/2008 | Hurst | A01G 7/045 362/231 |
| 2010/0020536 | A1 * | 1/2010 | Bafetti | F21K 9/20 362/231 |
| 2010/0107491 | A1 * | 5/2010 | Wilson | A01G 7/045 47/58.1 LS |
| 2010/0115830 | A1 * | 5/2010 | Dube | A01G 7/045 47/17 |
| 2010/0281771 | A1 * | 11/2010 | Kudo | A01G 7/045 47/58.1 LS |
| 2010/0289411 | A1 * | 11/2010 | Smits | H05B 45/22 315/113 |
| 2011/0016785 | A1 * | 1/2011 | Yamada | A01G 7/045 47/1.01 R |
| 2011/0125296 | A1 * | 5/2011 | Bucove | A01G 7/045 700/90 |
| 2011/0163246 | A1 * | 7/2011 | Ishiwata | A01G 7/045 250/492.1 |
| 2012/0287617 | A1 * | 11/2012 | Mekhtarian | A01G 7/045 362/228 |
| 2013/0298445 | A1 * | 11/2013 | Aoki | A01G 7/045 43/132.1 |
| 2014/0215918 | A1 * | 8/2014 | Takeuchi | A01G 7/045 47/58.1 LS |
| 2014/0225003 | A1 * | 8/2014 | Koo | A01G 7/045 250/454.11 |
| 2014/0250778 | A1 * | 9/2014 | Suntych | A01G 7/045 47/1.4 |
| 2014/0273197 | A1 * | 9/2014 | Chen | A01G 7/00 435/292.1 |
| 2015/0068114 | A1 * | 3/2015 | Bullis | A01G 7/06 47/2 |
| 2015/0150195 | A1 * | 6/2015 | Grajcar | H05B 45/10 47/58.1 LS |
| 2015/0216130 | A1 * | 8/2015 | Grajcar | H05B 45/20 47/58.1 LS |
| 2016/0014974 | A1 * | 1/2016 | Grajcar | A01G 7/045 47/58.1 LS |
| 2016/0021830 | A1 * | 1/2016 | Johnson | A01G 7/06 47/17 |
| 2016/0327228 | A1 * | 11/2016 | Farkas | G02B 5/0284 |
| 2016/0366845 | A1 * | 12/2016 | Visser | A01G 24/00 |
| 2017/0000041 | A1 * | 1/2017 | Wargent | A01G 7/045 |
| 2017/0228480 | A1 * | 8/2017 | Yoshida | G06Q 50/02 |
| 2017/0347532 | A1 * | 12/2017 | Suntych | A01G 7/045 |
| 2018/0007838 | A1 * | 1/2018 | McCord | A01G 7/045 |
| 2018/0035616 | A1 * | 2/2018 | Wagner | H05B 45/10 |
| 2018/0235217 | A1 * | 8/2018 | Yamauchi | A01N 35/02 |

FOREIGN PATENT DOCUMENTS

| | | |
|---|---|---|
| JP | 2004283170 | 10/2004 |
| WO | WO 95/33374 | 12/1995 |

OTHER PUBLICATIONS

McKirdy et al. "First Report of Grapevine Downy Mildew (*Plasmopara viticola*) in Commercial Viticulture in Western Australia" Plant Dis. Mar. 1999;83(3):301. doi: 10.1094/PDIS.1999.83.3.301D. (Year: 1999).*

* cited by examiner

METHOD FOR STIMULATING THE RESISTANCE OF PLANTS TO BIOTIC STRESS BY UV RADIATION EXPOSURE

TECHNICAL FIELD OF THE INVENTION

The present invention relates to a method for stimulating the resistance of plants to biotic stress by radiation exposure.

The invention will find an application in agriculture and for the food industry to avoid or at least reduce the use of pesticides. The invention stimulates natural defenses of plants to biotic stress such as pests, bacteria, fungus or virus. The invention could be used directly on plants growing in particular in the field, in greenhouses, in parks or natural areas.

STATE OF THE ART

During their lifetime, plants are exposed to some form of stress. Stresses can be abiotic (physical) such as cold, drought, heat, salinity or UV radiation or biotic (biological) such as fungi, oomycetes, bacteria, viruses, nematodes or phytophagous insects that perturb growth, development and reproduction of plants.

Each plant has certain environmental requirements for optimum growth, which can be reproduced quite easily, in fields or in greenhouses.

Nevertheless, the existing protection of agricultural crops against infections and damages caused by biotic stresses is seen as insufficient in agriculture. In particular, infection by fungi can result in severe harvest losses.

The fight against biotic stresses uses essentially pesticides such as fungicides that are a major source of environmental pollution. In the context of the reduction of marketing authorizations at EU level, there is the need to find alternatives to pesticides.

Among all UV radiations, only the amounts of UV-A and UV-B radiations reaching the earth surface will increase in the future. UV-C radiations, because of their high absorption level by the ozone layer, do not penetrate to the earth in any appreciable amount. This explains why a lot of research has been done on the biological effects and the mechanisms of action of UV-B and UV-A radiations during the two last decades, whereas UV-C radiations were neglected.

It appears from studies made on UV-B radiations that they are not only important as a part of the global change issue (i.e. because they carry potential negative effects on plant functioning and crop productivity), but also because they could be exploited for agronomic purposes. Positive effects of UV-B radiations encompass indeed such important topics as disinfection, the stimulation of the secondary metabolism, including the production of health-promoting phytochemicals, the stimulation of the so-called plant natural defenses, etc. . . . . There is however a major problem associated with UV-B radiations: UV-B radiations are generally effective only when they are delivered over rather extensive periods of time, typically several hours or days. It is very difficult to consider exploiting them in practical terms.

UV-C (Ultraviolet C) light is also known for disinfecting, sterilizing water or surfaces or for treating post-harvest plant materials such as harvested fruits and vegetables, which have been removed from the living/growing/photosynthesizing plants.

However, the application of high doses of UV-C on plants can alter their photosynthetic system and their growth.

In fact, WO95/33374 discloses a method for the destruction of vegetation at places where said vegetation is undesirable.

Thus, the object of the invention is to provide a method to fight against biotic stresses without using pesticides or allowing a limited use of such chemicals, compatible with plant growth and crop performance.

SUMMARY OF THE INVENTION

According to one aspect, the invention more particularly relates to a method for stimulating the resistance of plants to biotic stress by radiation exposure of at least one spot of a plant characterized in that the radiation exposure is performed by UV-C rays alone or UV-B rays alone or combination thereof, preferably the radiation exposure is to performed by UV-C rays alone or in combination with UV-B rays with an exposure duration being less or equal to one second and the radiation exposure being repeated at least once with an interval of time between 1 hour and 1 month.

The present invention has the advantage to expose the plant to very short UV-C radiations named flashes. Short exposure reduces the risk to alter or damage the plant, in particular its photosynthetic system. Surprisingly, short exposures to UV-B are also efficient to stimulate plant natural defenses.

In addition, flashes of UV-C and/or UV-B are repeated at least once with a specific interval of time. This repetition improves the effect of the stimulation of the plant resistance.

DRAWINGS

The aims and objects as well as the features and advantages of the invention will emerge more clearly from the detailed description of an embodiment of the latter that is illustrated by the following accompanying drawings, in which:

FIG. 4: Effect of exposure of tomato (*Ananas* variety) to standard pulsed light and filtered pulsed light (UV-C spectrum) for a single exposure and repeated exposures.

The drawings are given by way of examples and are not limitative of the invention.

DETAILED DESCRIPTION OF THE INVENTION

Advantageous embodiments are now disclosed prior to disclosing a detailed to description of an exemplary embodiment of the invention. These embodiments may be taken separately or in combination.

The invention relates to a method for stimulating the resistance of plants to biotic stress by radiation exposure comprising a radiation exposure which is performed by UV-C rays alone or UV-B rays alone or a combination thereof, with an exposure duration being less or equal to one second characterized in that the radiation exposure is performed at least on one spot of a plant and the radiation exposure being repeated at least once with an interval of time between one hour and one month.

Advantageously, the radiation exposure is performed by UV-C rays alone.

Advantageously, the radiation exposure is performed by a combination of UV-C rays with UV-B rays.

Advantageously, the total area of spots exposed to radiation is between 1 cm$^2$ and 100 cm$^2$ per plant.

Advantageously, the total area of plant exposed to radiation represents at least 1% of the total surface of the plant.

Advantageously, the dose of radiation delivered to the plant upon one exposure is less than 10 kJ/m$^2$.

Advantageously, the dose of radiation delivered to the plant upon one exposure is less than a plant destructive dose of radiation.

Advantageously, the UV-C and/or UV-B are produced by at least one of a light emitting diode or a xenon light source.

Advantageously, the UV-C rays have a wavelength between 230 nm and 279 nm.

Advantageously, the UV-C rays have a wavelength of 262+/−5 nm.

Advantageously, the exposure is repeated at least once within 48 hours following the first exposure.

Advantageously, the exposure is repeated at least four times, with an exposure every 48 hours.

Advantageously, the plant is a growing plant.

Advantageously, the plant is chosen from lettuce, pepper, wheat, maize, sorghum, soja, vine, tomato.

Advantageously, the plant is chosen from *Lactuva sativa*, scarole, vine.

Advantageously, the radiation exposure is continuous or pulsed with several bursts.

Advantageously, biotic stress is due to living organisms from fungi, viruses, bacteria, and insects.

According to another aspect, the invention relates to a plant irradiated according to the method described above.

According to another aspect, the invention relates to a method for stimulating the resistance of plants to biotic stress by radiation exposure of at least one spot of a plant characterized in that the radiation exposure is performed by UV-C rays alone or UV-B rays alone or a combination thereof, preferably the radiation exposure is performed by UV-C rays alone or in combination with UV-B rays, with an exposure duration being less or equal to one second.

Advantageously, the radiation exposure is repeated at least once with an interval of time between one hour and one month.

The method of the invention for stimulating the resistance of plants to biotic stress comprises the exposure of at least a part of a plant to short and repeated UV-C radiation alone or UV-B radiation alone or a combination of UV-C and UV-B in a preferred embodiment, said part of a plant is exposed to UV-C radiation.

Stimulating the resistance of plants to biotic stress includes to improve, to enhance or to increase natural defenses of plants to biotic stressors.

Biotic stresses include fungi i.e. necrotrophic and biotrophic, oomycetes, bacteria, viruses, nematodes or insects.

The ultraviolet radiation comprises UV-A, UV-B and UV-C. The method of the invention uses UV-C with a wavelength between 230 and 279 nm, preferably between 254 and 265 nm and more preferably 262 nm and/or UV-B with a wavelength between 280 and 315 nm, preferably between 280 and 300 nm and more preferably 280 nm.

Advantageously, the combination of UV-B and UV-C can reinforce the stimulation of the natural defenses. Without being bond by a theory, UV-C and UV-B could reach different targets and therefore activate different signaling paths. Molecular receptors may be different for these different categories of wavelengths.

The method of the invention comprises an exposure of at least a part of the plant. The exposure is typically very short. The exposure duration is equal or less to 1 second. According to the invention, the exposure is repeated at least once with an interval of time between 1 hour and 1 month, preferably between 2 days and 2 weeks and more preferably of 8 days.

The exposures are separated by at least one hour.

According to an embodiment, the exposure is repeated from 2 to 6 times, preferably 4 times. Each exposure is for instance spaced of at least 24 hours to 60 hours, advantageously 48 hours.

The interval of time between successive exposures may be identical.

Saying in another way, the method of the invention comprises a stimulating step comprising a first exposure and at least another exposure of at least a part of the plant. Each exposure lasts less than or are equal to 1 second. The stimulating step lasts from 1 hour to one month.

The first exposure and at least another exposure are performed within an interval of 1 hour to one month.

As the irradiation is very short, each exposure is also called a flash or shock irradiation.

The UV-C and/or UV-B are produced by light emitting diodes or xenon lamps. The source for the UV-C and/or UV-B can be monochromatic or filters could be used to select the wavelength(s) of interest. It is to be noted that according to the source the wavelength is set with a variation of more or less 2 to 20 nm, preferably 2 to 10 nm.

The exposure may be continuous or pulsed with several bursts during the exposure, the total time of exposure being less than 1 second. In particular, light emitting diodes provide continuous light and xenon lamps provide pulsed light.

According to a first embodiment, the method comprises several UV-C radiation exposures with a specific time interval.

According to a second embodiment, the method comprises several UV-B radiation exposures with a specific time interval.

According to a third embodiment, the method comprises several UV-C and UV-B radiation exposures and with a specific time interval. Each exposure comprises UV-C and UV-B, more precisely each exposure only comprises UV-C and UV-B and no other wavelengths.

According to a fourth embodiment, the method comprises at least one UV-C radiation exposure and at least one UV-B radiation exposure with a specific time interval between them.

Preferably, the dose of energy delivered to the plant is less than 10 kJ/m$^2$, preferably, the dose is less than 5 kJ/m$^2$, and preferably, the dose is less than or equal to 1 kJ/m$^2$. This energy is preferably delivered with one exposure. The doses for UV-B radiations, normalized at 300 nm, are advantageously similar to UV-C radiations.

Advantageously, the exposition is performed at least on a spot of the plant. A spot of the plant is a part, an area or a zone of the plant receiving the irradiation. The total surface of the plant receiving the irradiation represents at least 1% of the total surface of the plant. It is not necessary to expose 100% of the surface of the plant to irradiation to stimulate natural plant defenses. Preferably, the surface exposed is at least 1 cm$^2$ per plant. The surface exposed is advantageously, equal or less than 100 cm$^2$ per plant.

The part of the plant exposed is preferably leaves and/or fruits.

The surface exposed is determined by the real surface of the plant that received the irradiation.

The plants that could benefit of the method of the invention include, without being exhaustive, fruits, vegetables, seeds, trees . . . , in particular, lettuce, wheat, maize, rice, sorghum, soja, vine, tomato and pepper, more particularly *Lactuva sativa*, var *romana* and Scarola.

According to the invention, the plants, objects of the method, are growing. The method is not performed on post-harvest plants but could be. Preferably, the plants are growing in the field or in greenhouses. The plants are living plants or plant parts.

The method of the invention significantly improves the natural defenses of plants treated. Examples below show this improvement. The repetition of the exposure shows an unattended synergic effect of increasing the resistance of the plants.

In addition, only one part of the plant needs to be exposed to irradiation to improve the natural defenses of the whole plant. The parts, which are not exposed to irradiation, have also enhanced resistance there of showing a systemic effect of the method of the invention.

To implement the method, an illumination device is used. The device comprises a spectrally adjustable radiance source, advantageously based on light emitting diodes (LEDs). The source is based on LEDs and beam-integrating device to create a spatially uniform quasi-monochromatic light source. The light source with adjustable output port is illuminated using thermally stabilized narrow-band LEDs covering the wavelength of the irradiation needed. Advantageously, the device comprises a cooling system at the back of LEDs. For example, the LED modules are mounted inside aluminum or brass blocks. The temperatures of the aluminum or brass blocks are controlled using Peltier elements. To implement the method directly on plants growing in the field or in greenhouses, the lamps can be placed on illuminating devices that are either fixed or mobile.

EXAMPLES

In examples 1 to 3, the exposure to UV-C is performed at a dose of 1 kJ/m2 on 5 cm$^2$ of leaf surface from 4 week-old plants. Inoculation of pathogens is performed 48 hours after the treatment.

Example 1

5 cm$^2$ of leaves of romaine lettuce are exposed to UV-C for 1 minute or for 1 second at equal wavelength and energy. The romain lettuce is inoculated with *Botrytis cinerea* 48 hours after the exposure.

Figure 1:
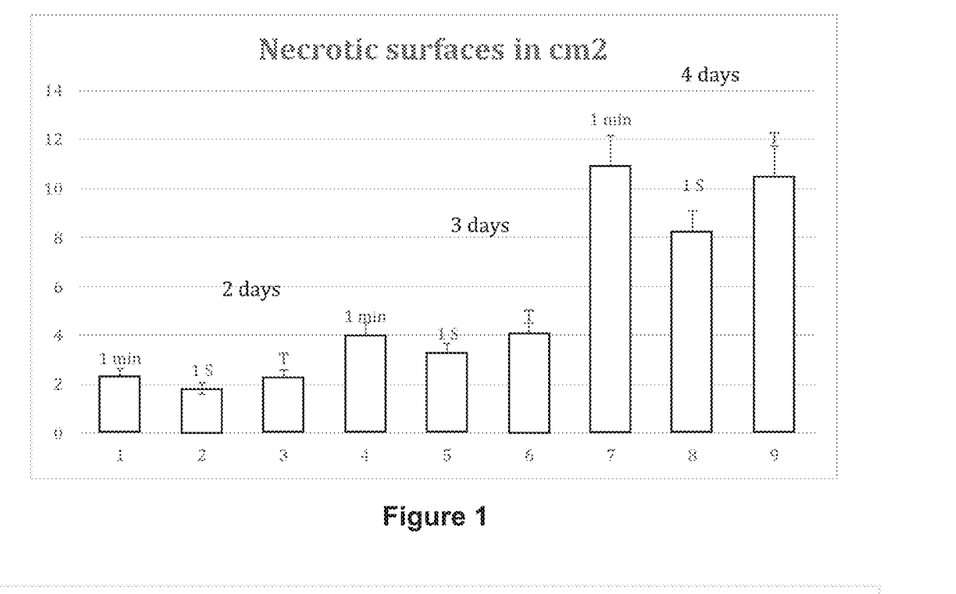
FIG. 1: Effect of a single exposure of romaine lettuce to 262 nm UV-C radiation for 1 minute and for 1 second at equal wavelength and energy, followed by inoculation with *Botrytis cinerea*.

Observations of the progression of lesions were conducted on leaves near to the treated leaves 2 days, 3 days and 4 days after inoculation. Evolution of necrotic surfaces in cm$^2$ is shown on FIG. 1. After 4 days, the necrotic surface is 5% lower in lettuce treated with an exposure of 1 minute whereas it is 21% lower in lettuce treated with an exposure of 1 second. The irradiation exposure of 1 second is more effective to improve the resistance of plants than the irradiation exposure of 1 minute. In addition, surprisingly, the plant is less damaged with a short exposure than with a long exposure, both delivering the same energy.

Example 2

5 cm$^2$ of leaves of pepper are exposed to UV-C for 1 minute or for 1 second at equal wavelength and energy. 48 hours after the exposure the pepper is inoculated with *Phytophtora capsici*.

Figure 2:
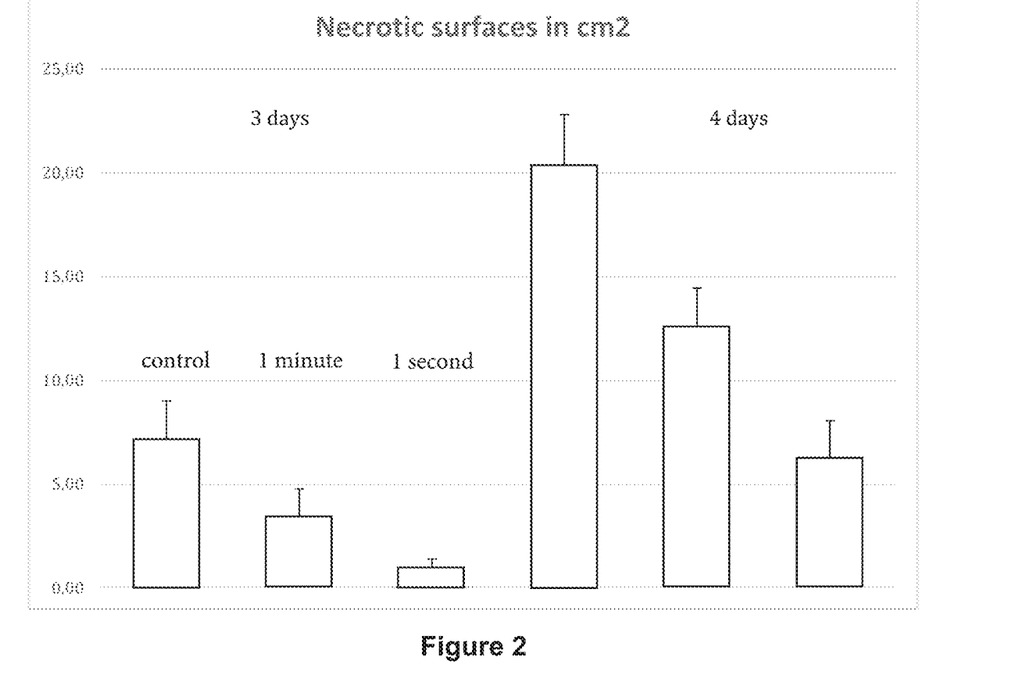
FIG. 2: Effect of a single exposure of pepper to 262 nm UV-C radiation for 1 minute and for 1 second, at equal wavelength and energy, followed by inoculation with *Phytophthora capsici*.

Observations of the progression of lesions were conducted on near leaves of the treated leaves 3 days and 4 days after inoculation. Evolution of necrotic surfaces in cm$^2$ is shown on FIG. 2. After 4 days, the necrotic is 38% lower in pepper treated with an exposure of 1 minute whereas it is 69% lower in pepper treated with an exposure of 1 second. The irradiation exposure of 1 second is more effective to improve the resistance of plants that the irradiation exposure of 1 minute.

The method of the invention seems even more effective against biotrophic than against necrotrophic fungi.

Example 3

5 cm$^2$ of leaves of romaine lettuce are exposed to UV-C for 1 second repeated 4 times with an interval of 48 hours. 48 hours after the last exposure the romain lettuce is inoculated with *Botrytis cinerea*.

Figure 3:
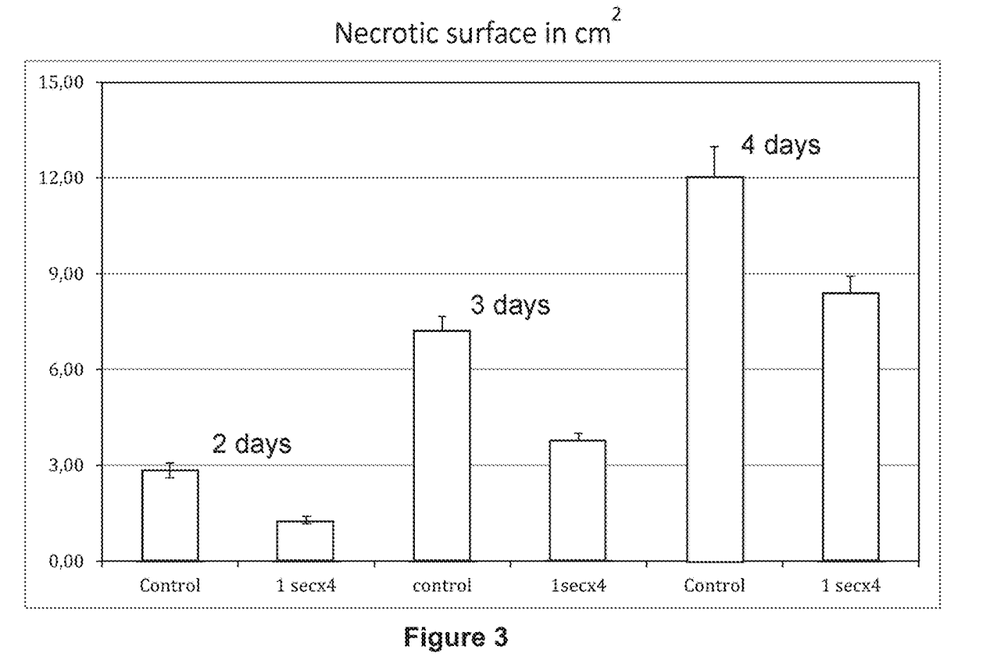
FIG. 3: Effect of exposure of romaine lettuce to 262 nm UV-C radiation for 1 second, with 4 repetitions, each at 2-day intervals, at equal wavelength and energy, followed by inoculation with *Botrytis cinerea*.
Figure 4A:
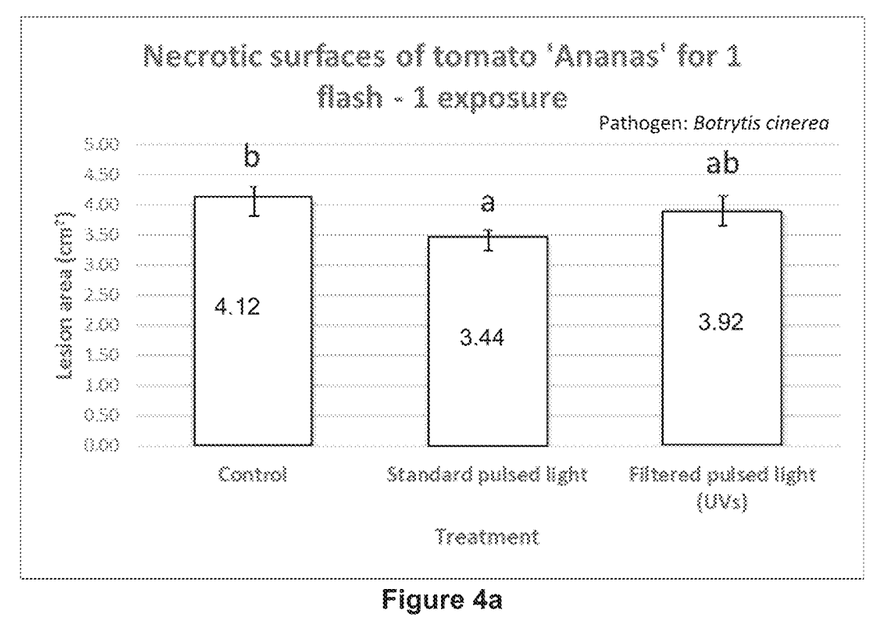
FIG. 4a: One single exposure.
Figure 4B:
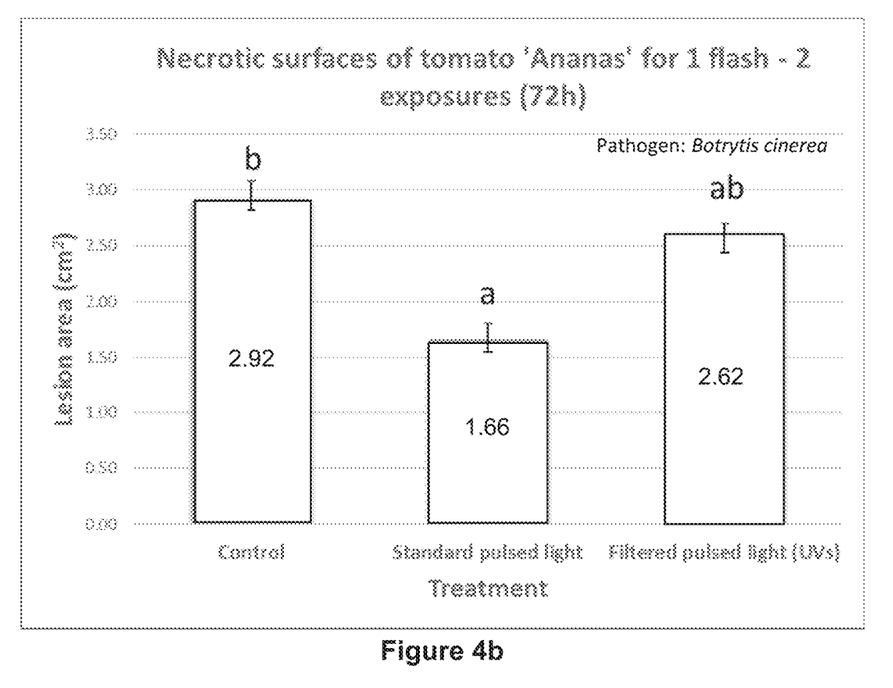
FIG. 4b: 2 exposure repetitions with 3-day intervals.
Figure 4C:
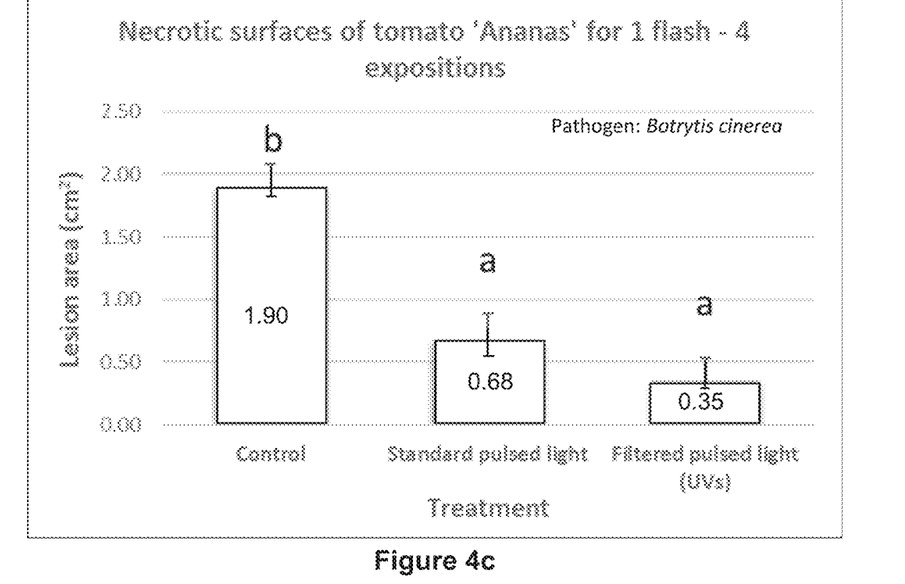
FIG. 4c: 4 exposure repetitions with 2-day intervals. All exposure are followed by inoculation with *Botrytis cinerea*.
Figure 5:
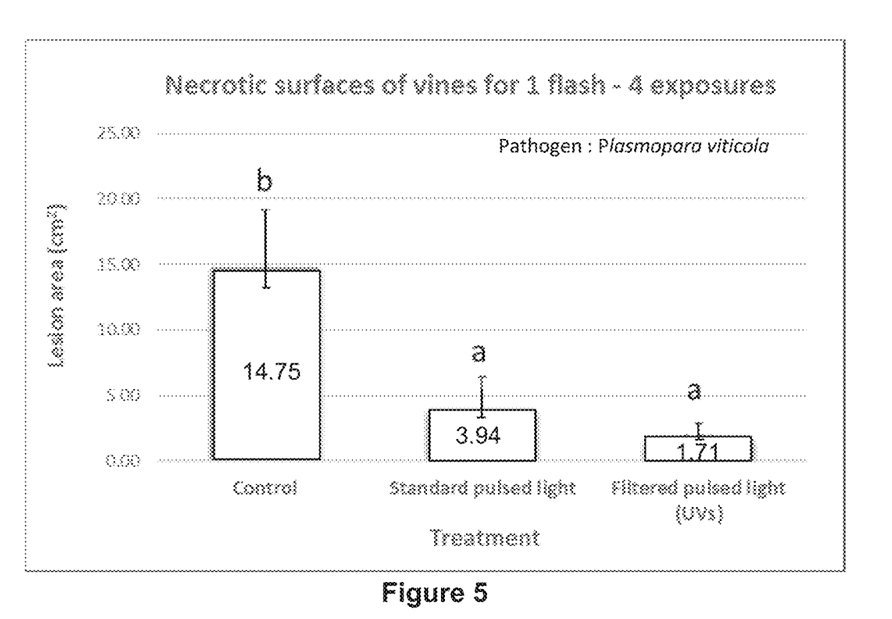
FIG. 5: Effect of exposure of vine to standard pulsed light and filtered pulsed light (UVC spectrum) for 4 repetitions with 2-day intervals followed by inoculation with *Plasmopara viticola*.
Figure 6:
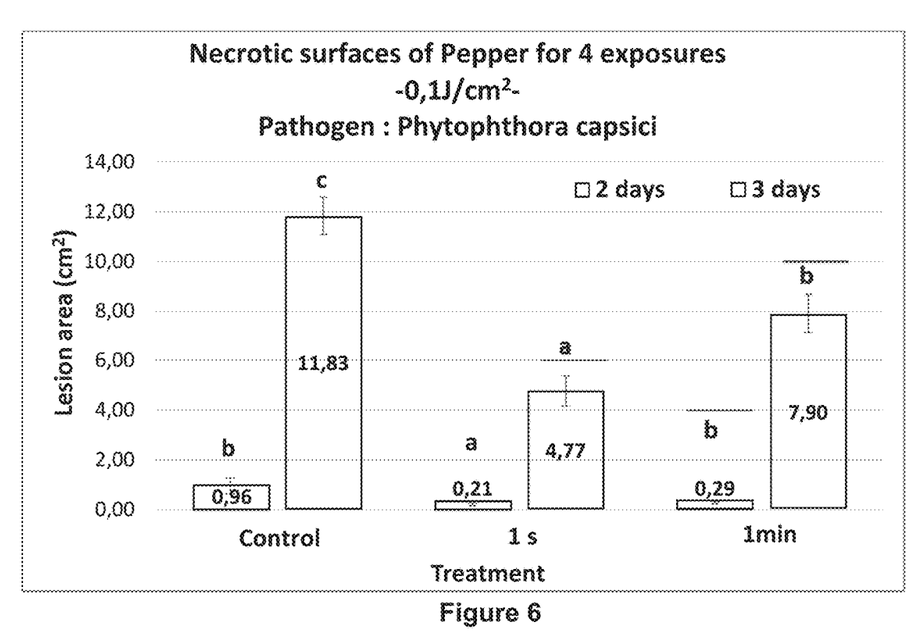
FIG. 6: Effect of exposure of pepper to 250-280 nm UV-C radiation for 1 minute and for 1 second, at equal wavelength and energy, repeated 4 times with 2-days intervals and followed by inoculation with *Phytophthora capsici*.
Figure 7:
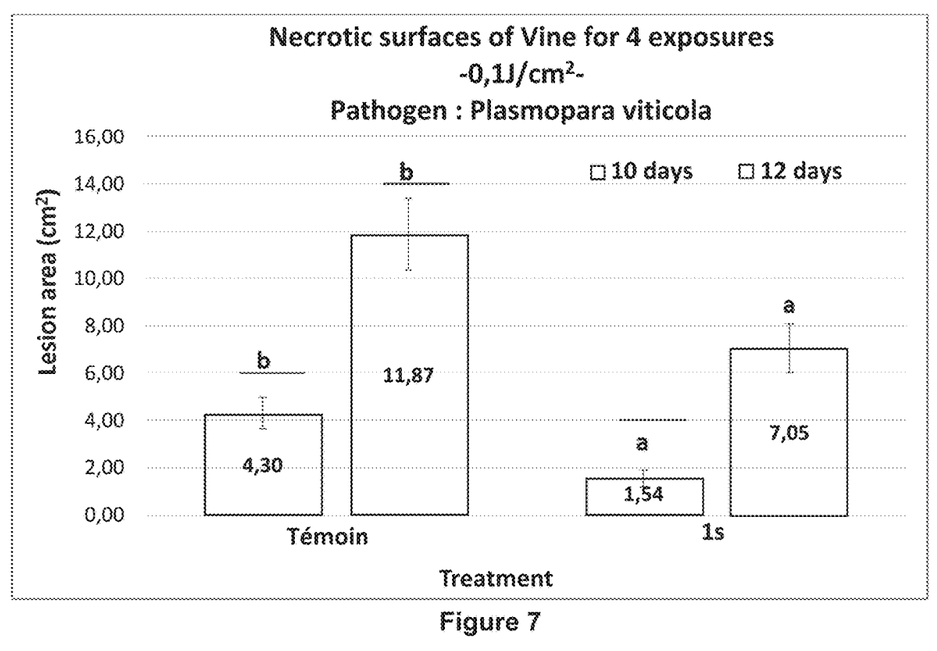
FIG. 7: Effect of exposure of vine to 250-280 nm UV-C radiation for 1 second repeated 4 times with 2-days intervals and followed by inoculation with *Plasmopara viticola*.
Figure 8:
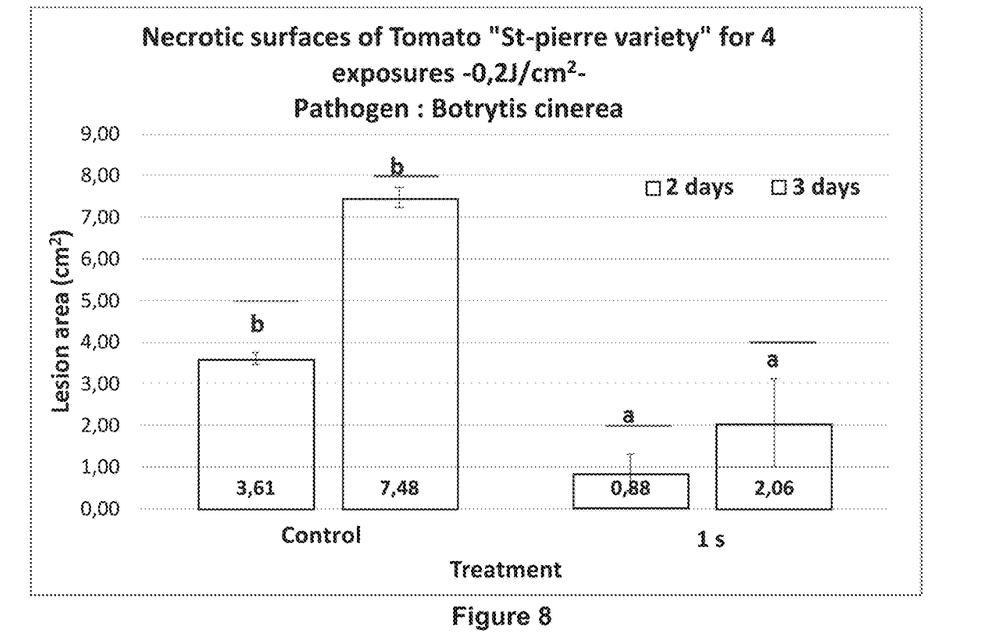
FIG. 8: Effect of exposure of tomato (Saint Pierre variety) to 250-280 nm UV-C radiation for 1 second with an energy of 0.2 J/cm$^2$, repeated 4 times with 2-day intervals and followed by inoculation with *Botrytis cinerea*.
Figure 9:
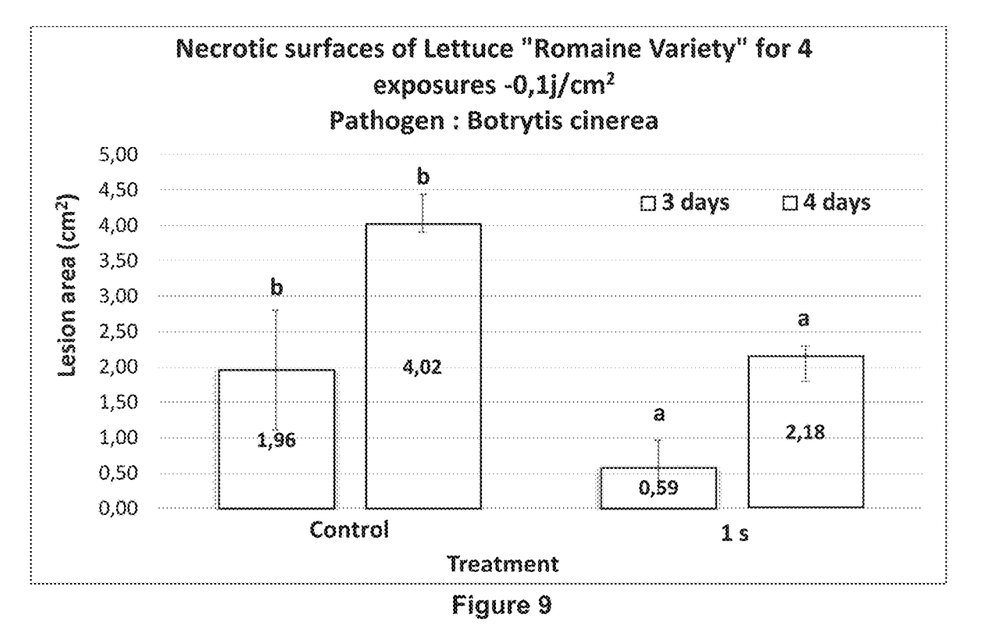
FIG. 9: Effect of exposure of romaine lettuce to 250-280 nm UV-C radiation for 1 second, with an energy of 0.1 J/cm$^2$, repeated 4 times with 2-day intervals and followed by inoculation with *Botrytis cinerea*.
Figure 10:
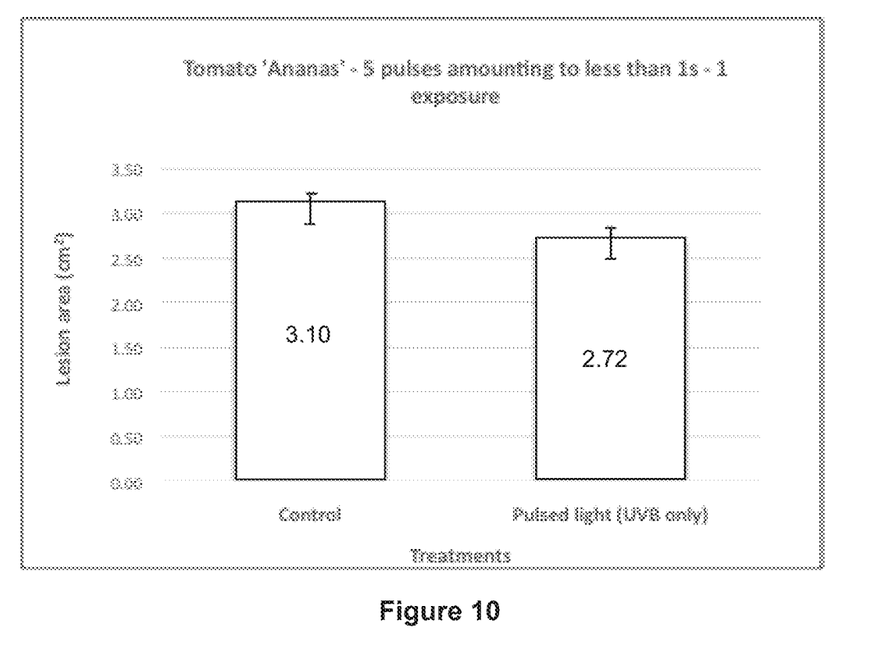
FIG. 10: Effect of exposure of tomato (*Ananas* variety) to filtered pulsed light (UV-B spectrum, 285 to 305 nm) for a single exposure consisting of 5 flashes of 300 microseconds each. Exposure is followed by inoculation with *Botrytis cinerea*.

Observations of the progression of lesions were conducted on leaves near to the treated leaves, 2 days, 3 days, 4 days and 5 days after inoculation. Evolution of necrotic surfaces in cm$^2$ is shown on FIG. 3. After 4 days, the necrotic surface is 31% lower in lettuce treated with an exposure of 1 second repeated.

The repetition of irradiation exposure brings an added value when compared to the absence of repetition (example 1): 31% reduction of lesion surface vs. 21%. The repetition of irradiation exposure of 1 second is more effective to improve the resistance of plants that the irradiation exposure of one exposure of 1 second.

In the two following examples, three light conditions were tested: control (no exposure to light), pulsed light exposure without filter and pulsed light exposure with a filter (trade UG5 filter, Schott©).

Pulsed light is generated with a xenon lamp. When the Xenon is excited by electrical discharges, it emits a light covering the visible spectrum but with more intense light emission in the blue and UV. The flashes used were generated by submitting an electric shock of 2500 volts during 300 microseconds. The exposure to UV-C is performed at a dose of 0.1 J/cm$^2$ (that is 1 kJ/m$^2$) (10% of UV-C in the total spectrum of the lamp).

The UG5 filter is a filter that doesn't let the visible light spectrum pass through and lets pass only all the UVs (with a percentage of transmission between 95 and 99%).

Example 4

8 cm$^2$ of leaves of tomato are exposed with pulsed light without filter and pulsed light with a filter.

Three cases were studied:
a first exposure followed by an inoculation with *Botrytis cinerea* 48 hours after the last exposure.
2 exposures with an interval of 72 hours followed by an inoculation with *Botrytis cinerea* 48 hours after the last exposure (on the same leaves);
4 exposures with an interval of 48 hours followed by an inoculation with *Botrytis cinerea* 48 hours after the last exposure (on different leaves);

The third case (4 exposures, one every two days) without filter and with filter allows a reduction of the surfaces infected by *Botrytis cinerea* of 64% and 82% respectively after 2 days.

Example 5

8 cm$^2$ of leaves of vine are exposed with pulsed light without filter, and pulsed light with a filter, repeated 4 times with an interval of 48 hours followed by a inoculation with *Plasmopara viticola* 48 hours after the last exposure.

This treatment without filter and with filter allows a reduction of the surfaces infected by *Plasmopara viticola* of 73% and 88% respectively.

Example 6

In the following example, the exposure to UV-C is performed at a dose of 0.1 J/cm$^2$ (that is 1 kJ/m$^2$). The pulsed light is obtained by using a 265 nm+/−15 nm (250-280 nm) UV-C LED.

5 cm$^2$ of leaves of pepper are exposed to UV-C for 1 second or for 1 minute at equal wavelength and energy. The exposure is repeated 4 times with an interval of 48 hours followed by an inoculation with *Phytophthora* 48 hours after the last exposure.

An exposure of 1 second allows a reduction of the surfaces infected of 59.7% and an exposure of 1 minute allows a reduction of 33.2% of the surfaces infected after 3 days.

For peppers leaves, the decreased sensitivity is more important for short-term exposure (1 second) compared to long-term exposure (1 minute).

Example 7

In the following example, the exposure to UV-C is performed at a dose of 0.1 J/cm$^2$ (that is 1 kJ/m$^2$). The pulsed light is obtained by using a 265 nm+/−15 nm (250-280 nm) UV-C LED.

5 cm$^2$ of leaves of *Vitis* are exposed to UV-C for 1 second. The exposure is repeated 4 times with an interval of 48 hours followed by a inoculation with *Plasmopara viticola* 48 hours after the last exposure.

An exposure of 1 second allows a reduction of the surfaces infected of 40.6% after 12 days.

Additional tests were performed on the two-follow species: tomato and lettuce. It was found that the stimulation of the tomato defenses requires a double dose of energy compared to lettuce, which it requires a single dose. The pulsed light is obtained by using a 265 nm+/−15 nm (250-280 nm) UV-C LED.

Example 8

5 cm$^2$ of leaves of tomato are exposed to UV-C for 1 second at a dose of 0.2 J/cm$^2$.

The exposure is repeated 4 times with an interval of 48 hours followed by an inoculation with *Botrytis cinerea* 48 hours after the last exposure.

An exposure of 1 second allows a reduction of the surfaces infected by *Botrytis cinerea* of 72% after 3 days.

Example 9

5 cm$^2$ of leaves of lettuce are exposed to UV-C for 1 second at a dose of 0.1 J/cm$^2$.

The exposure is repeated 4 times with an interval of 48 hours followed by an inoculation with *Botrytis cinerea* 48 hours after the last exposure.

An exposure of 1 second allows a reduction of the surfaces infected by *Botrytis cinerea* of 45% after 4 days.

Example 10

In the following example, an exposure to UV-B is performed at a dose of 0.1 j/cm$^2$ (that is 1 kJ/m$^2$). The pulsed light is obtained by using a 295 nm+/−10 nm (285-305 nm) UV-B LED.

8 cm$^2$ of leaves of tomato are exposed to UV-B for a single exposure consisting of 5 flashes of 300 microseconds each followed by a inoculation with *Botrytis cinerea* 48 hours after the last exposure.

This exposure allows a reduction of the surfaces infected by *Botrytis cinerea* of 12% after 2 days.

The invention claimed is:

1. A method for stimulating a resistance of plants to biotic stress, said method comprising:
    performing a radiation exposure by UV-C rays alone or UV-B rays alone or a combination thereof produced by a non-natural light source, with an exposure duration being less than or equal to one second,
    wherein
    the radiation exposure is performed on at least one spot of a plant,
    the radiation exposure is repeated at least once with an interval of time between one hour and one month, and
    a dose of radiation delivered to the plant upon one exposure is less than 10 kJ/m$^2$ and greater than 0.1 kJ/m$^2$.
2. The method according to claim 1, wherein the radiation exposure is performed by UV-C rays alone or a combination between UV-C rays and UV-B rays.
3. The method according to claim 1, wherein the radiation exposure is performed on one single spot of a plant.

4. The method according to claim 1, wherein the at least one spot represents a surface of the plant that is less than a total surface of the plant.

5. The method according to claim 1, wherein a total area of spots exposed to radiation is between 1 cm$^2$ and 100 cm$^2$ per plant.

6. The method according to claim 1, wherein a total area of plant exposed to radiation represents at least 1% of a total surface of the plant.

7. The method according to claim 1, wherein the dose of radiation delivered to the plant upon one exposure is less than 5 kJ/m$^2$.

8. The method according to claim 1, wherein the dose of radiation delivered to the plant upon one exposure is less than or equal to 1 kJ/m$^2$.

9. The method according to claim 1, wherein the dose of radiation delivered to the plant upon one exposure is less than a plant destructive dose of radiation.

10. The method according to claim 1, wherein at least one of the UV-C rays or UV-B rays are produced by the non-natural light source including at least one of a light emitting diode or a xenon light source.

11. The method according to claim 1, wherein the UV-C rays have a wavelength between 230 nm and 279 nm.

12. The method according to claim 1, wherein the UV-C rays have a wavelength of 262 nm.

13. The method according to claim 1, wherein the exposure is repeated at least once within 48 hours following the first exposure.

14. The method according to claim 1, wherein the exposure is repeated at least four times, with an exposure every 48 hours.

15. The method according to claim 1, wherein the plant is a growing plant.

16. The method according to claim 1, wherein the plant is chosen from lettuce, pepper, wheat, maize, sorghum, soja, vine, or tomato.

17. The method according to claim 1, wherein the plant is chosen from *Lactuca sativa*, scarole.

18. The method according to claim 1, wherein the biotic stress is due to at least one of living organisms including fungi, viruses, bacteria, and insects.

19. The method according to claim 1, wherein said plant is vine and said biotic stress is due to living *Plasmopara viticola*.

20. The method according to claim 1, wherein the radiation exposure is continuous or pulsed with several bursts.

* * * * *